United States Patent
Hirano et al.

(10) Patent No.: US 11,278,528 B2
(45) Date of Patent: Mar. 22, 2022

(54) ACTIVATOR OF PEROXISOME PROLIFERATOR-ACTIVATED RECEPTOR

(71) Applicant: Nippon Chemiphar Co., Ltd., Tokyo (JP)

(72) Inventors: Masuharu Hirano, Misato (JP); Takafumi Muto, Misato (JP)

(73) Assignee: Nippon Chemiphar Co., Ltd., Tokyo (JP)

( * ) Notice: Subject to any disclaimer, the term of this patent is extended or adjusted under 35 U.S.C. 154(b) by 0 days.

(21) Appl. No.: 16/762,981

(22) PCT Filed: Nov. 14, 2018

(86) PCT No.: PCT/JP2018/042133
§ 371 (c)(1),
(2) Date: May 11, 2020

(87) PCT Pub. No.: WO2019/098238
PCT Pub. Date: May 23, 2019

(65) Prior Publication Data
US 2020/0268719 A1    Aug. 27, 2020

(30) Foreign Application Priority Data

Nov. 15, 2017 (JP) .............................. JP2017-220362
Jul. 12, 2018 (JP) .............................. JP2018-132701

(51) Int. Cl.
*A61K 31/428* (2006.01)
*A61P 13/02* (2006.01)
(Continued)

(52) U.S. Cl.
CPC .......... *A61K 31/428* (2013.01); *A61K 31/192* (2013.01); *A61K 31/277* (2013.01); *A61P 13/02* (2018.01)

(58) Field of Classification Search
CPC .. A61K 31/428; A61K 31/192; A61K 31/277; A61P 13/02; A61P 1/00;
(Continued)

(56) References Cited

U.S. PATENT DOCUMENTS

2008/0194564 A1*  8/2008  Zeiller ................... C07C 59/72
                                                          514/239.2
2013/0150381 A1*  6/2013  Ouk et al. ............. C07C 323/53
                                                          514/262.1
2017/0290795 A1* 10/2017  Endo ...................... A61K 31/47

FOREIGN PATENT DOCUMENTS

JP      S48054047 A    7/1973
JP      S51012618 B2   4/1976
(Continued)

OTHER PUBLICATIONS

I. Issemann et al., Nature, 347, pp. 645-650, 1990.
(Continued)

*Primary Examiner* — Taylor V Oh
(74) *Attorney, Agent, or Firm* — Wood Herron & Evans LLP (57) ABSTRACT

There is provided an activator of peroxisome proliferator-activated receptor α which contains: a compound represented by the following Formula (I); a tautomer or stereoisomer of the compound; or a pharmaceutically acceptable
(Continued)

salt or solvate thereof (where, in a case where $R^1$, $R^2$, $R^3$, and $R^8$ do not constitute a ring, in the Formula, $R^1$, $R^2$, $R^3$, $R^6$, $R^7$, and $R^8$ may be the same as or different from each other and represent a hydrogen atom, a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group, or a cyano group).

14 Claims, 2 Drawing Sheets

(51) Int. Cl.
*A61K 31/192* (2006.01)
*A61K 31/277* (2006.01)

(58) Field of Classification Search
CPC ...... A61P 1/04; A61P 1/16; A61P 1/18; A61P 3/00; A61P 3/04; A61P 3/06; A61P 3/10; A61P 5/38; A61P 5/48; A61P 7/00; A61P 7/02; A61P 9/04; A61P 9/10; A61P 9/12; A61P 11/06; A61P 13/12; A61P 17/00; A61P 17/02; A61P 17/06; A61P 17/10; A61P 17/14; A61P 19/02; A61P 25/00; A61P 25/28; A61P 29/00; A61P 35/00; A61P 43/00
USPC .......................................... 514/367
See application file for complete search history.

(56) References Cited

FOREIGN PATENT DOCUMENTS

| | | |
|---|---|---|
| JP | S54081244 A | 6/1979 |
| JP | 2007536290 A | 12/2007 |
| JP | 2013530186 A | 7/2013 |
| WO | 2016108282 A1 | 7/2016 |

OTHER PUBLICATIONS

S. A. Kliewer et al., Proc. Natl. Acad. Sci. USA, vol. 91, pp. 7355-7359, 1994.
O. Braissant et al., Endocrinology, vol. 137, No. 1, pp. 354-366, 1996.
N. Tanaka et al., The Lipid, vol. 27, No. 4, pp. 336-371, 2016.
Y. Kohjimoto et al., Metabolic Syndrome and Nephrolithiasis, Hinyokika Kiyo, vol. 57, No. 1, pp. 43-47, 2011.
Naim M. Maalouf et al., Clin J Am Soc Nephrol, vol. 5, pp. 1277-1281, 2010.
S. Takahashi et al., Relationship between acidic urine and insulin resistance in gout patients-effect of bezafibrate treatment, Gout and Nucleic Acid Metabolism, vol. 30, No. 2, pp. 211-215, 2006.
T. Takada, Uric Acid transporterand disease, Farumashia, vol. 48, No. 12, pp. 1144-1148, 2012.
PCT Office, International Search Report issued in PCT/JP2018/042133 dated Feb. 19, 2019, 8 pages.
Alessandra Ammazzalorso et al: "Benzothiazole-based-(phenylsulfonyl)amides as a novel family of PPAR antagonists", Bioorganic & Medicinal Chemistry Letters, vol. 21, No. 16, Jun. 8, 2011 (Jun. 8, 2011), pp. 4869-4872, XP028267766.
Dusica Vidovi & Cacute; et al: "A Combined Ligand-and Structure-Based Virtual Screening Protocol Identifies Submicromolar PPAR[gamma] Partial Agonists", Chemm Edchem, vol. 6, No. 1, Jan. 3, 2011 (Jan. 3, 2011), pp. 94-103, XP55130644.
European Patent Office, Search Report issued in EP 18879461.4 dated Jul. 12, 2021.

* cited by examiner

ACTIVATOR OF PEROXISOME PROLIFERATOR-ACTIVATED RECEPTOR

TECHNICAL FIELD

The present invention relates to an activator of peroxisome proliferator-activated receptor α.

This application claims priority based on Japanese Patent Application No. 2017-220362 filed in Japan on Nov. 15, 2017 and Japanese Patent Application No. 2018-132701 filed in Japan on Jul. 12, 2018, of which the contents are incorporated herein by reference.

BACKGROUND ART

The peroxisome is an organelle found in cells of plants and animals, and its matrix contains various enzymes such as catalase. A peroxisome proliferator is a substance that induces proliferation of the peroxisome. Administration of therapeutic drugs for hyperlipidemia (fibrates), herbicides, phthalate plasticizers or the like is known to induce proliferation of the peroxisome and expression of genes such as catalase.

Isseman et al. have identified a nuclear receptor which is activated by the peroxisome proliferator and given a name of peroxisome proliferator-activated receptor (hereinafter, "PPAR") (Non-Patent Document 1).

As PPAR, three subtypes such as PPARα, PPARγ, and PPARδ have been identified until now (Non Patent Document 2). It has been reported that among them, PPARα is highly expressed in organs such as kidney, liver, heart, and skeletal muscle that consume large amounts of fatty acids (Non Patent Document 3).

The above-mentioned fibrates have a ligand effect on the PPARα and show a strong serum TG (triglyceride) lowering effect, and thus are used as therapeutic drugs for hyperlipidemia.

As fibrates, for example, clinofibrate represented by the following formula (Patent Literature 1),

[Chem. 1]

fenofibrate represented by the following formula (Patent Literature 2),

[Chem. 2]

and bezafibrate represented by the following formula (Patent Literature 3)

[Chem. 3]

are known.

Further, it has been reported that PPARα is related to, for example, arterial sclerosis or obesity, diabetes, metabolic syndrome, heart failure, and chronic kidney disease in addition to hyperlipidemia (Non Patent Literature 4), and is expected as a therapeutic/preventive drug for these diseases. Furthermore, these diseases are often accompanied by aciduria, and are known to increase the risk of urolithiasis, particularly uric acid calculi (Non Patent Literatures 5 and 6). However, it has also been reported that the fibrates have an effect of reducing aciduria (Non Patent Literature 7).

Incidentally, the present inventors have found that a derivative represented by the following formula inhibits reabsorption of uric acid via a uric acid transporter URAT1, and is useful as an agent for preventing or treating gout or hyperuricemia, and filed a patent application (Patent Literature 4):

[Chem. 4]

in the formula, a dotted line represents a single bond or a double bond,

Q represents $CR^8$, $NR^9$, or N, in a case where Q represents $CR^8$, $R^3$ and $R^8$ are bonded to each other to form a naphthalene ring or a quinoline ring together with a ring formed of dotted lines, or a combination of $R^1$ and $R^2$, $R^2$ and $R^8$, or $R^3$ and $R^8$ are bonded to each other to form a 5-membered heteroaryl ring containing 1 to 3 heteroatoms, as a ring constituent element, selected from a nitrogen atom, an oxygen atom, and a sulfur atom together with two carbon atoms to which the combination is bonded, and the heteroaryl ring forms a fused ring together with the ring formed of dotted lines, where, the ring formed of dotted lines is a ring in which the number of double bonds in the ring is the maximum, in a case where Q represents N, $R^1$ and $R^2$ are bonded to each other to form a quinoline ring together with the ring formed of dotted lines, in a case where Q represents $NR^9$, $R^3$ and $R^9$ or $R^2$ and $R^9$ are bonded to each other to form an imidazo[1,2-a]pyridine ring together with the ring formed of dotted lines, in a case where $R^1$, $R^2$, $R^3$, and $R^8$ do not constitute a ring, $R^1$, $R^2$, $R^3$, and $R^8$ may be the same as or different from each other and represent a hydrogen atom, a halogen atom, an alkyl group having 1 to 8 carbon atoms, a 3- to 7-membered cycloalkyl group, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, an alkenyl group having 2 to 8 carbon atoms, an alkynyl group having 2 to 8 carbon atoms, an alkylamino group having 1 to 8 carbon atoms, a dialkylamino group having 2 to 12 carbon atoms, an alkyloxycarbonyl group in which the alkyl group has 1 to 8 carbon atoms, a hydroxy group, an amino group, a carboxyl group, a nitro group, a cyano group, CONR'R", SR', or $SO_2$NR'R", where, R' and R" may be the same as or different from each other and represent a hydrogen atom or an alkyl group having 1 to 8 carbon atoms, in a case where $R^1$, $R^2$, $R^3$, and $R^8$ constitute a ring, the ring may have 1 to 4 substituents which are the same as the substituent for $R^1$ in the case where $R^1$, $R^2$, $R^3$, and $R^8$ do not constitute a ring, the substituents being the same as or different from each other, A represents a phenyl group, a naphthyl group, a pyridyl group, a pyrimidyl group, a pyrazyl group, a pyridazyl group, a quinolyl group, or an isoquinolyl group which may have 1 to 5 substituents same as that of $R^1$ in the case where $R^1$ does not constitute a ring, the substituents may be the same as or different from each other, where, A is bonded to the ring formed of dotted lines through a carbon atom constituting the ring of the A group, X represents $NR^{11}$, an oxygen atom, or a sulfur atom, where, $R^{11}$ represents a hydrogen atom, an alkyl group having 1 to 8 carbon atoms, or an alkyl group having 1 to 8 carbon atoms substituted with 1 to 3 halogen atoms, Y represents an alkylene chain having 1 to 8 carbon atoms, where, the alkylene chain may be substituted with 1 to 4 same or different groups selected from an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a 3- to 7-membered cycloalkyl group, or a 4- to 7-membered saturated hetero ring having 1 or 2 heteroatoms, as a ring constituent element, selected from an oxygen atom, a sulfur atom, and a nitrogen atom, the alkylene chain may be a linear or branched alkylene chain, the branched alkylene chain may have a 3-to 7-membered ring formed by side chains bonded to same carbon atom or different carbon atoms, together with the or each carbon atom to which the side chains are bonded, and the alkylene chain may have a double bond in the chain thereof in a case where the alkylene chain is an alkylene chain having 2 to 8 carbon atoms, and Z represents $CO_2H$, $CON(R^{12})$ $(R^{13})$, $CO_2(R^{14})$, $SO_2N(R^{15})$ $(R^{16})$ or a tetrazolyl group, where, $R^{12}$, $R^{14}$, and $R^{15}$ represent a hydrogen atom, an alkyl group having 1 to 8 carbon atoms or an alkyl group having 1 to 8 carbon atoms substituted with 1 to 3 halogen atoms, $R^{13}$ and $R^{16}$ represent a hydrogen atom, an alkyl group having 1 to 8 carbon atoms, an alkyl group having 1 to 8 carbon atoms substituted with 1 to 3 halogen atoms, a phenyl group which may have a substituent, a pyridyl group which may have a substituent, a pyridazyl group, a pyrimidyl group or a pyrazyl group, or a 5-membered heteroaryl ring containing 1 to 3 heteroatoms, as a ring constituent element, selected from a nitrogen atom, an oxygen atom, and a sulfur atom which may have a substituent, and where, in a case where $R^3$ and $R^8$ are bonded to each other to form a naphthalene ring together with the ring formed of dotted lines, X represents an oxygen atom, A represents a naphthalene, and the 1-position of A is bonded to the ring formed of dotted lines, the 2-position of A does not represent any of an alkoxy group having 1 to 8 carbon atoms, a hydroxy group, and ethyl 3-[[1-(2-fluorophenyl)naphthalen-2-yl]thio]propanoate.

However, the patent literatures do not clearly disclose that these compounds have an effect of activating peroxisome proliferator-activated receptor. Further, a uric acid excretion promoter having a mechanism of inhibition of URAT1 or the like has a risk of uric acid calculi because it promotes excretion of uric acid in urine, and there is a concern about the fact that the risk increases in the case of aciduria.

CITATION LIST

Patent Literature

Patent Literature 1: JP 48-54047 A
Patent Literature 2: JP 54-81244 A
Patent Literature 3: JP 51-12618 B
Patent Literature 4: WO 2016/108282 A Non Patent Literature Non Patent Literature 1: Nature, 347, p645-650, 1990
Non Patent Literature 2: Proc. Nati. Acad. Sci. USA, 91, p 7335-7359, 1994
Non Patent Literature 3: Endocrinology, 137, p354-366, 1996
Non Patent Literature 4: The Lipid, Vol. 27, No. 4, P336-371, 2016
Non Patent Literature 5: ACTA UROLOGICA JAPONICA, Vol. 57, No. 1, P 43-47, 2011
Non Patent Literature 6: Clin J Am Soc Nephrol, Vol. 5, P 1277-1281, 2010
Non Patent Literature 7: Gout and Nucleic Acid Metabolism, vol. 30, No. 2, P 211-215, 2006

SUMMARY OF INVENTION

Technical Problem

An object of the present invention is to provide an agent for treating or preventing a disease such as hyperlipidemia, dyslipidemia or diabetes which is mediated by a peroxisome proliferator-activated receptor α and having an excellent activating effect of peroxisome proliferator-activated receptor α.

Solution to Problem

The present inventors have conducted intensive studies and, as a result, have found that a compound having a URAT1 inhibitory activity disclosed in Patent Literature 4 has an excellent peroxisome proliferator-activated receptor α activating effect, and have completed the present invention.

That is, the present invention has the following aspects.

(1) An activator of peroxisome proliferator-activated receptor α including: a compound represented by the following Formula (I), a tautomer or stereoisomer of the compound, or a pharmaceutically acceptable salt or solvate thereof:

[Chem. 5]

where, in a case where $R^1$, $R^2$, $R^3$, and $R^8$ do not constitute a ring, in the formula, $R^1$, $R^2$, $R^3$, $R^6$, $R^7$, and $R^8$ may be the same as or different from each other and represent a hydrogen atom, a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group, or a cyano group, in a case where $R^1$, $R^2$, $R^3$, and $R^8$ constitute a ring, a combination of $R^1$ and $R^2$, $R^2$ and $R^8$, or $R^3$ and $R^8$ are bonded to each other to form a benzene ring, a pyridine ring, or a 5-membered heteroaryl ring containing 1 to 3 heteroatoms, as a ring constituent element, selected from a nitrogen atom, an oxygen atom, and a sulfur atom together with two carbon atoms to which the combination is bonded, where, the benzene ring, the pyridine ring, and the heteroaryl ring may be unsubstituted or may have 1 to 4 same or different substituents selected from a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group, or a cyano group, $R^4$ and $R^5$ are bonded to each other to form a benzene ring together with two carbon atoms to which $R^4$ and $R^5$ are bonded, or represent the same as that of $R^1$, where, the benzene ring may be unsubstituted or may have 1 to 4 same or different substituents selected from a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group, or a cyano group, W represents $CR^9$ or N,
where, $R^9$ represents the same as that of $R^1$,
X represents $NR^{10}$, an oxygen atom or a sulfur atom, where, $R^{10}$ represents a hydrogen atom, an alkyl group having 1 to 8 carbon atoms, or an alkyl group having 1 to 8 carbon atoms substituted with 1 to 3 halogen atoms, Y represents an alkylene chain having 1 to 8 carbon atoms or an alkenylene chain having 2 to 6 carbon atoms, where, the alkylene chain and the alkenylene chain may be unsubstituted or substituted with 1 to 4 groups selected from an alkyl group having 1 to 8 carbon atoms, an alkoxy group having 1 to 8 carbon atoms, an alkyl group having 1 to 8 substituted with 1 to 3 halogen atoms, or an alkoxy group having 1 to 8 carbon atoms substituted with 1 to 3 halogen atoms, the alkylene chain may be a linear or branched alkylene chain and the branched alkylene chain may have a 3- to 7-membered ring formed by side chains bonded to same carbon atom or different carbon atoms, together with the or each carbon atom to which the side chains are bonded and may have a double bond in the chain thereof in a case where the alkylene chain is an alkylene chain having 2 to 8 carbon atoms, Z represents $CO_2H$, $CO^2R^{11}$, a tetrazolyl group, or $SO_2NR^{12}R^{13}$, where, $R^{11}$ represents an alkyl group having 1 to 8 carbon atoms, and $R^{12}$ and $R^{13}$ may be the same as or different from each other and represent a hydrogen atom, an alkyl group having 1 to 8 carbon atoms, or an alkyl group having 1 to 8 carbon atoms substituted with 1 to 3 halogen atoms, where, in a case where $R^3$ and $R^8$ are bonded to each other to form a benzene ring together with two carbon atoms to which $R^3$ and $R^3$ are bonded, X represents an oxygen atom, $R^4$ and $R^5$ are bonded to each other to form a benzene ring together with two carbon atoms to which $R^4$ and $R^5$ are bonded, $R^7$ represents neither an alkoxy group having 1 to 8 carbon atoms nor a hydroxy group.

(2) The activator of peroxisome proliferator-activated receptor α according to (1), including: the compound, a tautomer or stereoisomer of the compound, or a pharmaceutically acceptable salt or solvate thereof, where $R^3$ and $R^3$ are bonded to each other to form a benzene ring or a pyridine ring together with two carbon atoms to which $R^3$ and $R^3$ are bonded.

(3) The activator of peroxisome proliferator-activated receptor α according to (1), including: the compound, a tautomer or stereoisomer of the compound, or a pharmaceutically acceptable salt or solvate thereof, where $R^3$ and $R^8$ together with two carbon atoms to which $R^3$ and $R^8$ are bonded form a 5-membered heteroaryl ring containing two heteroatoms, as a ring constituent element, selected from a nitrogen atom, an oxygen atom, and a sulfur atom.

(4) The activator of peroxisome proliferator-activated receptor α according to (1) or (3), including: the compound; a tautomer or stereoisomer of the compound; or a pharmaceutically acceptable salt or solvate thereof, where $R^3$ and $R^8$ together with two carbon atoms to which $R^3$ and $R^8$ are bonded form thiazole ring or isothiazole.

(5) The activator of peroxisome proliferator-activated receptor α according to any one of (1) to (4), including: the compound; a tautomer or stereoisomer of the compound; or a pharmaceutically acceptable salt or solvate thereof, where $R^1$, $R^2$, $R^6$, and $R^7$ may be the same as or different from each other and represent a hydrogen atom, a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, or a cyano group.

(6) The activator of peroxisome proliferator-activated receptor α according to any one of (1) to (5), including: the compound, a tautomer or stereoisomer of the compound, or a pharmaceutically acceptable salt or solvate thereof, where $R^6$ is a halogen atom, an alkyl group having 1 to 8 carbon atoms substituted with 1 to 3 halogen atoms, or a cyano group.

(7) The activator of peroxisome proliferator-activated receptor α according to any one of (1) to (6), including: the compound, a tautomer or stereoisomer of the compound, or a pharmaceutically acceptable salt or solvate thereof, where W represents CH.

(8) The activator of peroxisome proliferator-activated receptor α according to any one of (1) to (7), including: the compound, a tautomer or stereoisomer of the compound, or a pharmaceutically acceptable salt or solvate thereof, where X represents an oxygen atom or a sulfur atom.

(9) The activator of peroxisome proliferator-activated receptor α according to any one of (1) to (8), including: the compound, a tautomer or stereoisomer of the compound, or a pharmaceutically acceptable salt or solvate thereof, where Y is represented by the following Formula (II),

[Chem. 6]

(II)

in the formula, $R^a$ and $R^b$ may be the same as or different from each other and represent an alkyl group having 1 to 8 carbon atoms, or $R^a$ and $R^b$ are bonded to each other to form a 3- to 7-membered cycloalkane together with carbon atoms to which $R^a$ and $R^b$ are bonded, and "–" represents a bond.

(10) The activator of peroxisome proliferator-activated receptor α according to any one of (1) to (9), including: the compound, a tautomer or stereoisomer of the compound, or a pharmaceutically acceptable salt or solvate thereof, where Z represents $CO_2H$.

(11) A method for treating and/or preventing a disease mediated by a peroxisome proliferator-activated receptor α, including administering a therapeutically effective amount of the compound according to any one of (1) to (10) or a salt thereof to a patient in need thereof.

(12) The treating and/or preventing method according to (11), where the disease mediated by the peroxisome proliferator-activated receptor α represents hyperlipidemia, dyslipidemia, hypercholesterolemia, hypertriglyceridemia, hypo-HDL-cholesterolemia, hyper-LDL-cholesterolemia, non-HDL-cholesterolemia, hyper-VLDL-cholesterolemia, lipoprotein dysfunction, low levels of apolipoprotein A-I in the blood, atherosclerosis, atherosclerotic disease, coronary artery disease, cerebrovascular disorder, peripheral vascular disorder, metabolic syndrome, syndrome X, obesity including visceral fat obesity, diabetes, hyperglycemia, insulin resistance, impaired glucose tolerance, hyperinsulinemia, diabetic complication, heart failure, myocardial infarction, cardiomyopathy, hypertension, chronic kidney disease, fatty liver, non-alcoholic steatohepatitis, thrombus, Alzheimer's disease, neurodegenerative disease, demyelinating disease, multiple sclerosis, adrenoleukodystrophy, dermatitis, psoriasis, acne, skin aging, abnormal hair growth, inflammation, arthritis, asthma, irritable bowel syndrome, ulcerative colitis, Crohn's disease, pancreatitis, and cancer including colon cancer, bowel cancer, skin cancer, breast cancer, prostate cancer, ovarian cancer, and lung cancer.

(13) The treating and/or preventing method according to (11) or (12), where the disease mediated by the peroxisome proliferator-activated receptor α represents various types of dyslipidemias, metabolic syndrome, obesity including visceral fat obesity, atherosclerosis and related diseases thereof or diabetes.

(14) Use of the compound or a salt thereof according to any one of (1) to (10), for treating and/or preventing the disease mediated by the peroxisome proliferator-activated receptor α.

(15) The use according to (14), where the disease mediated by the peroxisome proliferator-activated receptor α represents hyperlipidemia, dyslipidemia, hypercholesterolemia, hypertriglyceridemia, hypo-HDL-cholesterolemia, hyper-LDL-cholesterolemia, non-HDL-cholesterolemia, hyper-VLDL-cholesterolemia, lipoprotein dysfunction, low levels of apolipoprotein A-I in the blood, atherosclerosis, atherosclerotic disease, coronary artery disease, cerebrovascular disorder, peripheral vascular disorder, metabolic syndrome, syndrome X, obesity including visceral fat obesity, diabetes, hyperglycemia, insulin resistance, impaired glucose tolerance, hyperinsulinemia, diabetic complication, heart failure, myocardial infarction, cardiomyopathy, hypertension, chronic kidney disease, fatty liver, non-alcoholic steatohepatitis, thrombus, Alzheimer's disease, neurodegenerative disease, demyelinating disease, multiple sclerosis, adrenoleukodystrophy, dermatitis, psoriasis, acne, skin aging, abnormal hair growth, inflammation, arthritis, asthma, irritable bowel syndrome, ulcerative colitis, Crohn's disease, pancreatitis, and cancer including colon cancer, bowel cancer, skin cancer, breast cancer, prostate cancer, ovarian cancer, and lung cancer.

(16) The use according to (14) or (15), where the disease mediated by PPAR represents various types of dyslipidemias, metabolic syndrome, obesity including visceral fat obesity, atherosclerosis and related diseases thereof or diabetes.

(17) A method for improving aciduria including administering an effective amount of the compound or a salt thereof according to (1) to (10) for improving aciduria associated with the disease mediated by the peroxisome proliferator-activated receptor α.

(18) Use of the compound or a salt thereof according to (1) to (10), for improving aciduria associated with the disease mediated by the peroxisome proliferator-activated receptor α.

(19) The method according to (17), for treating and/or preventing urolithiasis and uric acid calculi.

(20) The method according to (18), for treating and/or preventing urolithiasis and uric acid calculi.

(21) The method according to claim (17) or (19), for treating and/or preventing renal disorder due to urolithiasis and uric acid calculi.

(22) The use according to claim (18) or (20), for treating and/or preventing renal disorder due to urolithiasis and uric acid calculi.

DESCRIPTION OF EMBODIMENTS

Subsequently, the present invention will be described in detail.

In the present specification, examples of the alkyl group having 1 to 8 carbon atoms represented by $R^1$ to $R^{13}$, $R^a$ and $R^b$ include a methyl group, an ethyl group, a propyl group, an iso-propyl group, a butyl group, an iso-butyl group, a tert-butyl group, a pentyl group or a hexyl group, and preferably an alkyl group having 1 to 3 carbon atoms such as a methyl group, an ethyl group, and a propyl group.

Examples of the alkyl group having 1 to 8 carbon atoms substituted with 1 to 3 halogen atoms represented by $R^1$ and $R^{13}$ include the alkyl group substituted with 1 to 3 halogen atoms such as a fluorine atom, a chlorine atom or a bromine atom, preferably a trifluoromethyl group, a chloromethyl group, a 2-chloroethyl group, a 2-bromoethyl group or a 2-fluoroethyl group, and more preferably a trifluoromethyl group.

Examples of the alkoxy group having 1 to 8 carbon atoms represented by $R^1$ to $R^9$ include a methoxy group, an ethoxy group, a propoxy group, an isopropoxy group, a butoxy group, an iso-butoxy group, a tert-butoxy group, a pentyloxy group or a hexyloxy group, and preferably a methoxy group, an ethoxy group, a propoxy group, and a butoxy group.

Examples of the alkoxy group having 1 to 8 carbon atoms substituted with 1 to 3 halogen atoms represented by $R^1$ to $R^9$ include a methoxy group, an ethoxy group, a propoxy group, an iso-propoxy group, a butoxy group or a tert-butoxy group, all of which are substituted with 1 to 3 halogen atoms such as a fluorine atom, a chlorine atom or a bromine atom, and preferably a trifluoromethoxy group, a chloromethoxy group, a 2-chloroethoxy group, a 2-bromoethoxy group or a 2-fluoroethoxy group.

Examples of the alkylsulfanyl group represented by $R^1$ to $R^9$ include a linear or branched chain alkylsulfanyl group having 1 to 8 carbon atoms, such as a methylsulfanyl group, an ethylsulfanyl group, a propylsulfanyl group, a butylsulfanyl group, an iso-butylsulfanyl group, and a tert-butylsulfanyl group, and preferably a methylsulfanyl group and an ethylsulfanyl group.

Examples of the halogen atom represented by $R^1$ to $R^9$ include a fluorine atom, a chlorine atom, a bromine atom, and an iodine atom, and preferably a fluorine atom and a chlorine atom.

In a case where $R^1$, $R^2$, $R^3$, and $R^8$ constitute a ring, it is preferable that a combination of $R^3$ and $R^8$ be bonded to each other. In such a case, $R^3$, $R^8$, and two carbon atoms to which $R^3$ and $R^8$ are bonded to each other to form a 5-membered heteroaryl ring containing 1 to 3 heteroatoms, as a ring constituent element, selected from a nitrogen atom, an oxygen atom, and a sulfur atom, and in that case, examples of the heteroaryl ring include thiazole, isothiazole, oxazole, isoxazole, and 2,1,3-thiadiazole, and preferably thiazole and isothiazole.

In a case where $R^1$, $R^2$, $R^3$, and $R^8$ constitute a ring, examples of substituents on the benzene ring, the pyridine ring, and the heteroaryl ring include 1 to 4 same or different halogen atoms, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group or a cyano group, preferably, a halogen atom, an alkyl group having 1 to 8 carbon atoms, an alkoxy group having 1 to 8 carbon atoms, an alkyl group having 1 to 8 carbon atoms substituted with 1 to 3 halogen atoms, a hydroxy group, an amino group, a carboxyl group, a mercapto group, a nitro group or a cyano group, and more preferably, an alkyl group having 1 to 8 carbon atoms, and an alkyl group having 1 to 8 carbon atoms substituted with 1 to 3 halogen atoms.

Examples of substituents on the benzene ring which may be formed by bonding $R^4$, $R^5$, and two carbon atoms to which $R^4$ and $R^5$ are bonded include 1 to 4 same or different halogen atoms, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group or a cyano group, preferably a halogen atom, an alkyl group having 1 to 8 carbon atoms, an alkoxy group having 1 to 8 carbon atoms, an alkyl group having 1 to 8 carbon atoms substituted with 1 to 3 halogen atoms, a hydroxy group, an amino group, a carboxyl group, a mercapto group, a nitro group or a cyano group, and more preferably a halogen atom, an alkyl group having 1 to 8 carbon atoms, and a hydroxy group.

Examples of the 3- to 7-membered cycloalkane represented by $R^a$ and $R^b$ bonded together with carbon atoms to which $R^a$ and $R^b$ are bonded include a cyclopropane ring, a cyclobutane ring, a cyclopentane ring and a cyclohexane ring, and preferably a cyclobutane ring and a cyclopentane ring.

Examples of the alkylene chain represented by Y include a linear or branched chain alkylene chain having 1 to 8 carbon atoms, such as methylene, ethylene, propylene, butylene, and iso-butylene, and preferably methylene, ethylene, and propylene.

The alkenylene chain represented by Y means a linear or branched chain alkenylene chain having 2 to 6 carbon atoms and having 1 to 3 double bonds, and examples thereof include vinylene, allylene, 1-propenylene, isopropenylene, 1-, 2- or 3-butenylene, and 1,3-butadienylene, and preferably vinylene and allylene.

Examples of substituents on the alkylene chain and alkenylene chain represented by Y include 1 to 4 alkyl groups having 1 to 8 carbon atoms, an alkoxy group having 1 to 8 carbon atoms, and an alkyl group having 1 to 8 carbon atoms substituted with 1 to 3 halogen atoms, an alkoxy group having 1 to 8 carbon atoms substituted with 1 to 3 halogen atoms, and preferably an alkyl group having 1 to 8 carbon atoms.

Further, the number of substituents is preferably 2.

In the branched chain alkylene chain represented by Y, a 3- to 7-membered ring formed by side chains bonded to same carbon atom or different carbon atoms, together with the or each carbon atom to which the side chains are bonded is, for example, cyclopropane, cyclobutane or cyclopentane.

Examples of a preferred aspect of the compound (I) used in the present invention include when W is $CR^9$, $R^1$, $R^2$, $R^4$, $R^5$, $R^7$, and $R^9$ are each a hydrogen atom, an alkyl group having 1 to 8 carbon atoms, a halogen atom, and a hydroxy group, $R^6$ is a halogen atom, an alkyl group having 1 to 8 carbon atoms substituted with 1 to 3 halogen atoms, and a cyano group, $R^3$, $R^8$, and two carbon atoms to which $R^3$ and $R^8$ are bonded to each other to form a 5-membered heteroaryl ring containing two heteroatoms, as a ring constituent element, selected from a nitrogen atom, an oxygen atom, and a sulfur atom, X is an oxygen atom or a sulfur atom, $R^a$ and $R^b$ in Y represent an alkyl group having 1 to 8 carbon atoms, and Z represents $CO_2H$.

Further, examples of a preferred aspect of the compound (I) used in the present invention include when W is $CR^9$, $R^1$, $R^4$, $R^5$, $R^7$, and $R^9$ are each a hydrogen atom, $R^2$ is a hydrogen atom or a fluorine atom, $R^6$ is a fluorine atom or a chlorine atom, a trifluoromethyl group, and a cyano group, a heteroaryl ring formed by joining $R^3$, $R^8$, and two carbon atoms to which $R^3$ and $R^8$ are bonded is a thiazole or isothiazole, X is a sulfur atom, $R^a$ and $R^b$ in Y represent an alkyl group having 1 to 3 carbon atoms, and Z represents $CO_2H$.

The salt of the Formula (I) is not particularly limited as long as it is a pharmaceutically acceptable salt. Examples thereof include a salt with a mineral acid such as hydrochloric acid or sulfuric acid; a salt with an organic carboxylic acid such as formic acid, acetic acid, citric acid, trichloroacetic acid, trifluoroacetic acid, fumaric acid or maleic acid; an acid addition salt such as a salt with a sulfonic acid such as methanesulfonic acid, benzenesulfonic acid, p-toluenesulfonic acid, mesitylenesulfonic acid or naphthalenesulfonic acid; a salt with an alkali metal such as lithium, sodium or potassium; a salt with an alkaline earth metal such as calcium or magnesium; an ammonium salt; and a base addition salt such as a salt with a nitrogen-containing organic base such as trimethylamine, triethylamine, tributylamine, pyridine, N,N-dimethylaniline, N-methylpiperidine, N-methylmorpholine, diethylamine, cyclohexylamine, procaine, dibenzylamine, N-benzyl-β-phenethylamine, 1-ephenamine or N,N'-dibenzylethylenediamine.

Further, the compound (I) may have stereoisomers such as cis-trans isomers, optically active isomers, and racemic isomers, all of which can be used in the present invention.

Furthermore, the compound (I) may be a tautomer, a hydrate, a solvate with an organic solvent such as alcohol, a derivative substituted with a stable isotope such as deuterium, or a prodrug.

The compound (I) used in the present invention can be produced by the method described in Patent Literature 4.

The compound (I) or a salt thereof can be used as an activator of peroxisome proliferator-activated receptor α to formulate a composition together with a pharmaceutically acceptable carrier for oral administration or the like in solid or liquid form.

Examples of solid formulations for oral administration include capsules, tablets, pills, powders, and granules. In preparing the solid formulations, the compound of the present invention is generally admixed with at least one inert diluent, for example, sucrose, lactose or starch. For the formulations or the usual formulation process, additional substances other than the inert diluent, such as lubricants (e.g., magnesium stearate), may be used. In the case of capsules, tablets, and pills, a buffer may be further used. Tablets and pills may be provided with an enteric coating.

Examples of liquid formulations for oral administration include inert diluents commonly used by those skilled in the art, e.g., pharmaceutically acceptable emulsions, solutions, suspensions, syrups, and elixirs containing water. In addition to such inert diluents, the composition can also include adjuvants such as wetting agents, emulsifying agents, and suspensions; and sweetening, flavoring, and perfuming agents.

The dose of the compound (I) of the present invention depends on the nature of the compound to be administered, the route of administration, the desired duration of treatment, and other factors, and is generally about 0.1 to 1000 mg/kg, and particularly preferably about 0.5 to 100 mg/kg per day for adults. If desired, the daily dose can be divided and administered in 2 or 4 doses.

EXAMPLES

Subsequently, the present invention will be described in more detail with reference to test examples, but the present invention is not limited thereto.

(Test Example 1)
(1) Measurement of Agonist Activity against PPARα

For the measurement of agonist activity against PPARα, the absorbance was measured according to the kit protocol using EnBio RCAS for PPARα kit (PPARA-CBP, Fujikura Kasei Co., Ltd.). A sample was dissolved in dimethylsulfoxide and added to a 96-well plate so as to have an evaluation concentration of 10 μM. GW7647 was added to a maximal response well so as to have a concentration of 0.5 μM. Dimethylsulfoxide was added to background wells. After subtracting the absorbance of the background well from the absorbance of each sample addition well, the ratio of each sample addition well to the maximal response well was calculated to evaluate the agonist activity (Binding ratio, %) against PPARα. Note that the sample addition wells and the background wells were duplicated, and the maximal response well was quadruplicated. As a positive control, 10 μM of a known PPARα agonist; Fenofibric acid (Tokyo Chemical Industry Co., Ltd.) was used.

Based on the above test, (COMPOUND 1) to (COMPOUND 17) in [Table 1-1] and [Table 1-2] were evaluated for agonist activity against PPARα.

TABLE 1-1

| Compound Nos. | Structural formula | Compound name |
|---|---|---|
| COMPOUND 1 |  | 2-[[7-(4-cyanophenyl)benzo[d]thiazol-6-yl]thio]-2-methylpropanoic acid |

TABLE 1-1-continued

| Compound Nos. | Structural formula | Compound name |
|---|---|---|
| COMPOUND 2 | | 2-[[7-(4-cyanophenyl)benzo[d]isothiazol-6-yl]thio]-2-methylpropanoic acid |
| COMPOUND 3 | | 2-[[6-(4-cyanophenyl)benzo[d]thiazol-5-yl]oxy]-2-methylpropanoic acid |
| COMPOUND 4 | | 2-[[1-(4-cyanophenyl)naphthalen-2-yl]thio]-2-methylpropanoic acid |
| COMPOUND 5 | | 2-[[7-(4-cyanophenyl)-3-methylbenzo[d]isothiazol-6-yl]thio]-2-methyl propanoic acid |
| COMPOUND 6 | | 2-[[7-(4-cyanophenyl)-2-(trifluoromethyl)benzo[d]thiazol-6-yl]thio]-2-methylpropanoic acid |

TABLE 1-1-continued

| Compound Nos. | Structural formula | Compound name |
|---|---|---|
| COMPOUND 7 | | 2-[[7-(4-cyanophenyl)-2-methylbenzo[d]thiazol-6-yl]thio]-2-methylpropanoic acid |
| COMPOUND 8 | | 1-[[7-(4-cyanophenyl)benzo[d]isothiazol-6-yl]thio]cyclobutan-1-carboxylic acid |
| COMPOUND 9 | | 2-methyl-2-[[7-[4-(trifluoromethyl)phenyl]benzo[d]isothiazol-6-yl]thio]propanoic acid |

TABLE 1-2

| Compound Nos. | Structural formula | Compound name |
|---|---|---|
| COMPOUND 10 | | 2-[[7-(4-cyanophenyl)-4-fluorobenzo[d]isothiazol-6-yl]thio]-2-methylpropanoic acid |
| COMPOUND 11 | | 1-[[7-(4-cyanophenyl)benzo[d]isothiazol-6-yl]thio]cyclopentan-1-carboxylic acid |

TABLE 1-2-continued

| Compound Nos. | Structural formula | Compound name |
|---|---|---|
| COMPOUND 12 | | 2-[[7-(4-chlorophenyl)benzo[d]isothiazol-6-yl]thio]-2-methylpropanoic acid |
| COMPOUND 13 | | 2-[[7-(4-cyano-3-methylphenyl)benzo[d]isothiazol-6-yl]thio]-2-methylpropanoic acid |
| COMPOUND 14 | | 1-[[7-(4-cyanophenyl)-3-methylbenzo[d]isothiazol-6-yl]thio]cyclobutan-1-carboxylic acid |
| COMPOUND 15 | | 2-[[7-(4-cyanophenyl)benzo[d]isothiazol-6-yl]thio]-2-ethylbutanoic acid |
| COMPOUND 16 | | 2-[[7-(4-cyanophenyl)benzo[d]isothiazol-6-yl]thio]-3,3-dimethylbutanoic acid |

TABLE 1-2-continued

| Compound Nos. | Structural formula | Compound name |
|---|---|---|
| COMPOUND 17 | | 1-[[7-(4-cyanophenyl)benzo[d]isothiazol-6-yl]thio]cyclohexan-1-carboxylic acid |
| Fenofibric acid (*1) | | 2-[4-(4-chlorobenzoyl)phenoxy]-2-methylpropionic acid |

(*1) Fenofibric acid is an active metabolite of fenofibrate.

(2) Test Results
Table 2 shows the test results.

TABLE 2

| Compound Nos. | Binding ratio (%) @ 10 μM |
|---|---|
| 1 | 49.17 |
| 2 | 69.85 |
| 3 | 16.04 |
| 4 | 52.63 |
| 5 | 41.83 |
| 6 | 24.71 |
| 7 | 47.03 |
| 8 | 29.87 |
| 9 | 86.96 |
| 10 | 71.35 |
| 11 | 21.66 |
| 12 | 92.56 |
| 13 | 20.76 |
| 14 | 26.50 |
| 15 | 58.96 |
| 16 | 11.79 |
| 17 | 13.51 |
| Fenofibric acid | 50.46 |

From the above results, it was confirmed that the compounds used in the present invention had an excellent PPARα activating effect.

(Test Example 2)
(1) Evaluation Using Non-Alcoholic Fatty Liver Disease (NAFLD) Model Rats Induced by Methionine/Choline-Deficient Diet As a NAFLD model, rats fed with a methionine/choline-deficient (MCD) diet were used to perform experiments. The MCD diet-fed model is widely used as a model for NAFLD/NASH.

Wistar rats (male, 8 weeks old, Charles River Laboratories Japan, Inc.) were fed with an MCD diet (A02082002B, Research Diets, Inc.) for 5 weeks. From the time of feeding the above diet for 1 week, the rats were divided into a Vehicle group, a COMPOUND 2 (50 mg/kg) group, and a Fenofibrate (100 mg/kg) group so that there was no difference in body weight between the groups (n=4 in each of the groups). The Normal group was fed with an MCS diet as a control diet for the MCD diet (A02082003B, Research Diets, Inc.) for the same period. The administration volume was 10 mL/kg, a 1% methylcellulose solution was repeatedly orally administered to the Vehicle group and the Normal group, and a COMPOUND 2 solution and a Fenofibrate solution were repeatedly orally administered to the COMPOUND 2 group and the Fenofibrate group, respectively, once a day for 4 weeks.

The day after the end of the final administration, blood was collected from the posterior vena cava under non-fasting conditions and isoflurane inhalation anesthesia, and plasma was collected. Further, the liver was removed and a part thereof was cryopreserved. Plasma ALT was measured by the JSCC standardized method. Triglyceride (TG) in the liver was extracted from the liver with a chloroform/methanol mixed solution (2:1, v/v), evaporated to dryness, and dissolved in 2-propanol, and then the amount was measured using Triglyceride E Test Wako. The results were each expressed as a mean value±standard deviation. Significant difference was tested between the Normal group and the Vehicle group using the Welch's t test (unpaired) (#: $p<0.05$ and ###: $p<0.001$), and significant difference was tested among the Vehicle group and the test substance administration groups using the Dunnett's test (*: $p<0.05$, : $p<0.01$, and *: $p<0.001$).

Figure 1A:
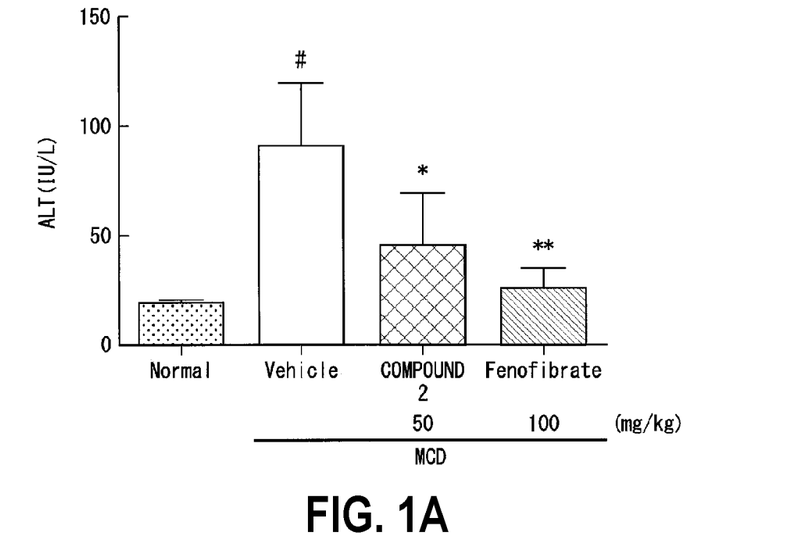
FIG. 1A is a diagram showing measurement results of plasma ALT as an indicator of liver damage in a test example.
Figure 1B:
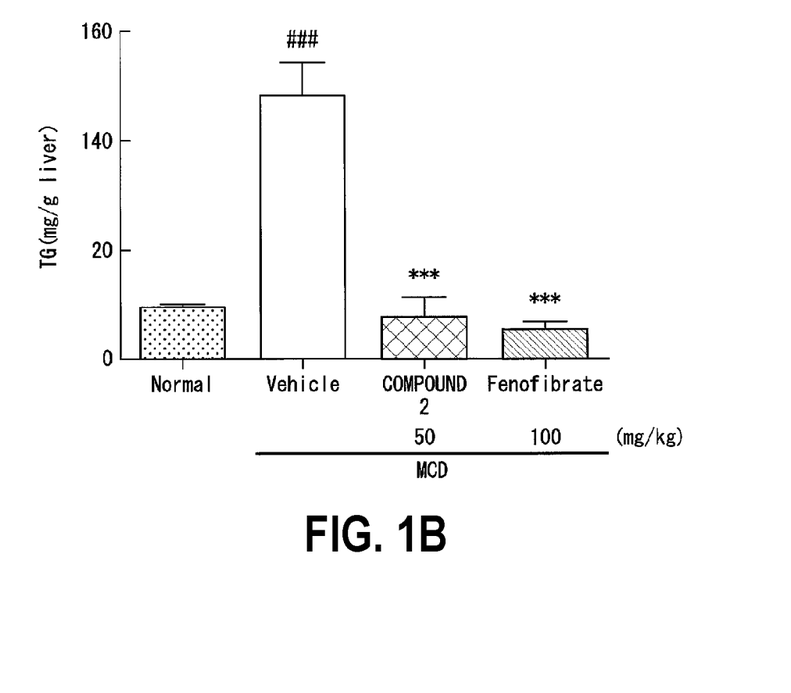
FIG. 1B is a diagram showing measurement results of liver TG level as an indicator of fatty liver in a test example.

(2) Test Results
The test results are shown in FIGS. 1A and 1B. Plasma ALT as an indicator of liver damage increased significantly in the Vehicle group fed with the MCD diet, compared to the Normal group fed with the MCS diet. On the other hand, the COMPOUND 2 group and the Fenofibrate group showed significantly lower values than the Vehicle group (FIG. 1A). Further, the liver TG level as an indicator of fatty liver increased significantly in the Vehicle group as compared to the Normal group, but was significantly lower in the COMPOUND 2 group and the Fenofibrate group than in the Vehicle group (FIG. 1B).

From these results, it was found that after repeated oral administration of the compound of the present invention to rats fed with the MCD diet, a decrease in plasma ALT and liver TG level was observed, and the compound had a NAFLD pathological ameliorating effect.

(Test Example 3)

(1) Evaluation Using Diabetic Models, Zucker Diabetic Fatty (ZDF) Rats

In this example, the low urinary pH improving effect of COMPOUND 2 was evaluated using diabetic model animals; ZDF rats with low urinary pH. Verinurad; a known URAT1 inhibitor was evaluated as a comparative control compound (the PPARα activating effect of Verinurad was evaluated by the method described in Test Example 1, and as a result, the binding ratio at an evaluation concentration of 10 μM was 3.80%, and no effect was confirmed).

ZDF (Lepr$^{fa}$/Lepr$^{fa}$) rats (male, 7 weeks old at the start of administration, Charles River Laboratories Japan, Inc.) were divided into a Vehicle group, a COMPOUND 2 (25 mg/kg) group, a COMPOUND 2 (50 mg/kg) group, and a Verinurad (50 mg/kg) group so that there was no difference in body weight between the groups (n=5 in each of the groups). As a Lean group, ZDF (Lean) rats, i.e., control animals of ZDF (Lepr$^{fa}$/Lepr$^{fa}$) rats, were used (n=5). The administration volume was 10 mL/kg, a 1% methylcellulose solution was repeatedly orally administered to the Vehicle group and the Lean group, and a COMPOUND 2 solutions and a Verinurad solution were repeatedly orally administered to the COMPOUND 2 groups and the Verinurad group, respectively, once a day for 15 days.

During the administration period, the pH of a urine sample obtained by urine collection was measured using a compact pH meter (B-712, Horiba, Ltd.). Urine collection was performed 6 days before the start of administration (pre), on the 1st day, 7th day and 14th day of administration, and urine was collected in a metabolic cage for 24 hours. The results were each expressed as a mean value±standard deviation. At each time point, significant difference was tested between the Lean group and the Vehicle group using the Student's t test (unpaired) (###: p<0.001). After one-way analysis of variance, significant difference was tested among the Vehicle group and the test substance administration groups using the Dunnett's test (*: p<0.05, : p<0.01, and *: p<0.001).

(2) Test Results

Figure 2:
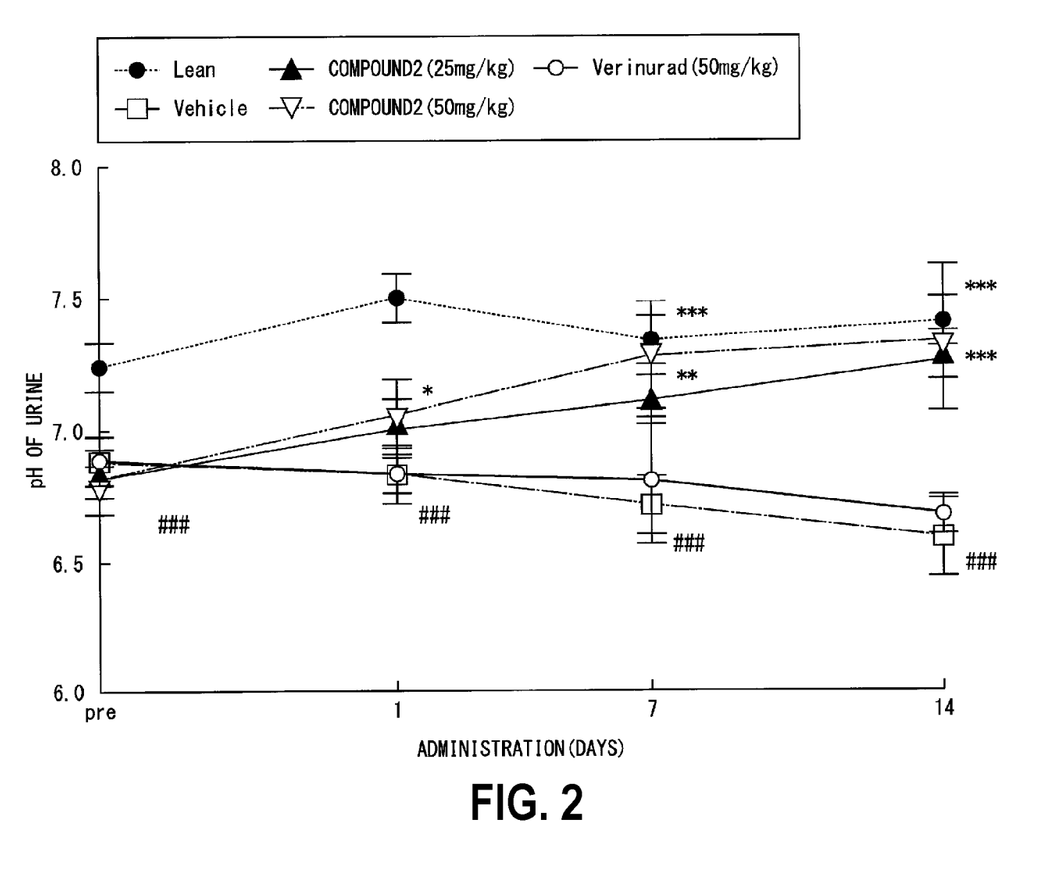
FIG. 2 is a diagram showing measurement results of urine pH as an indicator of diabetes in a test example.

FIG. 2 shows the test results. The Vehicle group had significantly lower urine pH than the Lean group throughout the test period from the start of administration, and exhibited low urinary pH. In the COMPOUND 2 groups, the urine pH was significantly increased from the 7th day of administration in the case of (25 mg/kg) and the urine pH was significantly increased from the 1st day of administration in the case of 50 mg/kg, compared to the Vehicle group, and this showed a dose-dependent low urinary pH improving effect. On the other hand, in the Verinurad group, no low urinary pH improving effect was observed throughout the administration period.

These results indicate that the compound of the present invention has a low urinary pH improving effect when orally administered to ZDF rats with low urinary pH.

The invention claimed is:

1. A method for treating fatty liver or chronic kidney disease, comprising administering a therapeutically effective amount of a compound represented by the following Formula (I) or a salt thereof to a patient in need thereof:

where,
where $R^1$, $R^2$, $R^3$, and $R^8$ constitute a ring, a combination of $R^1$ and $R^2$, $R^2$ and $R^8$, or $R^3$ and $R^8$ are bonded to each other to form a benzene ring, a pyridine ring, or a 5-membered heteroaryl ring containing 1 to 3 heteroatoms, as a ring constituent element, selected from a nitrogen atom, an oxygen atom, and a sulfur atom together with two carbon atoms to which the combination is bonded, provided that at least one combination of $R^1$ and $R^2$, $R^2$ and $R^8$, or $R^3$ and $R^8$ constitute the ring, and wherein, $R^1$, $R^2$, $R^3$, $R^6$, $R^7$, and $R^8$ may be the same as or different from each other and represent a hydrogen atom, a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group, or a cyano group, where, the benzene ring, the pyridine ring, and the heteroaryl ring may be unsubstituted or may have 1 to 4 same or different substituents selected from a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group, or a cyano group, $R^4$ and $R^5$ are bonded to each other to form a benzene ring together with two carbon atoms to which $R^4$ and $R^5$ are bonded, or represent the same as that of $R^1$, where, the benzene ring may be unsubstituted or may have 1 to 4 same or different substituents selected from a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group, or a cyano group, W represents $CR^9$ or N,
where, $R^9$ represents the same as that of $R^1$,
X represents $NR^{10}$, an oxygen atom or a sulfur atom, where, $R^{10}$ represents a hydrogen atom, an alkyl group having 1 to 8 carbon atoms, or an alkyl group having 1 to 8 carbon atoms substituted with 1 to 3 halogen atoms, Y represents an alkylene chain having 1 to 8 carbon atoms or an alkenylene chain having 2 to 6 carbon atoms, where, the alkylene chain and the alkenylene chain may be unsubstituted or substituted with 1 to 4 groups selected from an alkyl group having 1 to 8 carbon atoms, an alkoxy group having 1 to 8 carbon atoms, an alkyl group having 1 to 8 substituted with 1 to 3 halogen atoms, or an alkoxy group having 1 to 8 carbon atoms substituted with 1 to 3 halogen atoms, the alkylene chain may be a linear or branched alkylene chain and the branched alkylene chain may have a 3- to 7-membered ring formed by side chains bonded to same carbon atom or different carbon atoms, together with the or each carbon atom to which the side chains are bonded and may have a double bond in the chain thereof in a case where the alkylene chain is an alkylene chain having 2 to 8 carbon atoms, Z represents $CO_2H$, $CO^2R^{11}$, a tetrazolyl group, or $SO_2NR^{12}R^{13}$, where, $R^{11}$ represents an alkyl group having 1 to 8 carbon atoms, and $R^{12}$ and $R^{13}$ may be the same as or different from each other and represent a hydrogen atom, an alkyl group having 1 to 8 carbon atoms, or an alkyl group having 1 to 8 carbon atoms substituted wit 1 to 3 halogen atoms, where, in a case where $R^3$ and $R^8$ are bonded to each other to form a benzene ring together with two carbon atoms to which $R^3$ and $R^8$ are bonded, X represents an oxygen atom, $R^4$ and $R^5$ are bonded to each other to form a benzene ring together with two carbon atoms to which $R^4$ and $R^5$ are bonded, $R^7$ represents neither an alkoxy group having 1 to 8 carbon atoms nor a hydroxy group.

2. A method for improving aciduria comprising administering an effective amount of the compound or a salt thereof as defined in claim 1 for improving aciduria associated with the disease mediated by the peroxisome proliferator-activated receptor α.

3. The method according to claim 2, for treating urolithiasis and uric acid calculi.

4. The method according to claim 2, for treating renal disorder due to urolithiasis and uric acid calculi.

5. The method according to claim 1, wherein $R^3$ and $R^8$ are bonded to each other to form a benzene ring or a pyridine ring together with two carbon atoms to which $R^3$ and $R^8$ are bonded.

6. The method according to claim 1, wherein $R^3$ and $R^8$ are bonded to each other to form a 5-membered heteroaryl ring containing two heteroatoms, as a ring constituent element, selected from a nitrogen atom, an oxygen atom, and a sulfur atom, together with two carbon atoms to which $R^3$ and $R^8$ are bonded.

7. The method according to claim 1, wherein $R^3$ and $R^8$ are bonded to each other to form thiazole ring or isothiazole together with two carbon atoms to which $R^3$ and $R^8$ are bonded.

8. The method according to claim 1, wherein $R^1$, $R^2$, $R^6$, and $R^7$ may be the same as or different from each other and represent a hydrogen atom, a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, or a cyano group.

9. The method according to claim 1, wherein $R^6$ is a halogen atom, an alkyl group having 1 to 8 carbon atoms substituted with 1 to 3 halogen atoms, or a cyano group.

10. The method according to claim 1, wherein W represents CH.

11. The method according to claim 1, wherein X represents an oxygen atom or a sulfur atom.

12. The method according to claim 1, wherein Y is represented by the following Formula (II), (II)

in the formula, $R^a$ and $R^b$ may be the same as or different from each other and represent an alkyl group having 1 to 8 carbon atoms, or $R^a$ and $R^b$ are bonded to each other to form a 3- to 7-membered cycloalkane together with carbon atoms to which $R^a$ and $R^b$ are bonded, and "-" represents a bond.

13. The method according to claim 1, wherein Z represents $CO_2H$.

14. The method according to claim 1, wherein the compound is selected from 2-[[7-(4-cyanophenyl)benzo[d]thiazol-6-yl]thio]-2-methylpropanoic acid, 2-[[7-(4-cyanophenyl)benzo[d]isothiazol-6-yl]thio]-2-methylpropanoic acid, 2-[[6-(4-cyanophenyl)benzo[d]thiazol-5-yl]oxy]-2-methylpropanoic acid, 2-[[1-(4-cyanophenyl)naphthalen-2-yl]thio]-2-methylpropanoic acid, 2-[[7-(4-cyanophenyl)-3-methylbenzo[d]isothiazol-6-yl]thio]-2-methyl propanoic acid, 2-[[7-(4-cyanophenyl)-2-(trifluoromethyl)benzo[d]thiazol-6-yl]thio]-2-methylpropanoic acid, 2-[[7-(4-cyanophenyl)-2-methylbenzo[d]thiazol-6-yl]thio]-2-methylpropanoic acid, 1-[[7-(4-cyanophenyl)benzo[d]isothiazol-6-yl]thio]cyclobutan-1-carboxylic acid, 2-methyl-2-[[7-[4-(trifluoromethyl)phenyl]benzo[d]isothiazol-6-yl]thio]propanoic acid, 2-[[7-(4-cyanophenyl)-4-fluorobenzo[d]isothiazol-6-yl]thio]-2-methylpropanoic acid, 1-[[7-(4-cyanophenyl)benzo[d]isothiazol-6-yl]thio]cyclopentan-1-carboxylic acid, 2-[[7-(4-chlorophenyl)benzo[d]isothiazol-6-yl]thio]-2-methylpropanoic acid, 2-[[7-(4-cyano-3-methylphenyl)benzo[d]isothiazol-6-yl]thio]-2-methylpropanoic acid, 1-[[7-(4-cyanophenyl)-3-methylbenzo[d]isothiazol-6-yl]thio]cyclobutan-1-carboxylic acid, 2-[[7-(4-cyanophenyl)benzo[d]isothiazol-6-yl]thio]-2-ethylbutanoic acid, 2-[[7-(4-cyanophenyl)benzo[d]isothiazol-6-yl]thio]-3,3-dimethylbutanoic acid, and 1-[[7-(4-cyanophenyl)benzo[d]isothiazol-6-yl]thio]cyclohexan-1-carboxylic acid.

* * * * *